United States Patent
Hsieh et al.

(10) Patent No.: US 10,383,589 B2
(45) Date of Patent: Aug. 20, 2019

(54) DIRECT MONOCHROMATIC IMAGE GENERATION FOR SPECTRAL COMPUTED TOMOGRAPHY

(71) Applicant: General Electric Company, Schenectady, NY (US)

(72) Inventors: Jiang Hsieh, Brookfield, WI (US); Zhoubo Li, Libertyville, IL (US); Brian Edward Nett, Brookfield, WI (US); Meghan Lynn Yue, Johnson Creek, WI (US); Roy A. Nilsen, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/829,554

(22) Filed: Dec. 1, 2017

(65) Prior Publication Data
US 2019/0167218 A1    Jun. 6, 2019

(51) Int. Cl.
*A61B 6/00*    (2006.01)
*G06T 11/00*    (2006.01)
*A61B 6/03*    (2006.01)

(52) U.S. Cl.
CPC .............. *A61B 6/482* (2013.01); *A61B 6/032* (2013.01); *A61B 6/5241* (2013.01); *G06T 11/008* (2013.01)

(58) Field of Classification Search
CPC ...... A61B 6/032; A61B 6/5241; G06T 11/008
See application file for complete search history.

(56) References Cited

U.S. PATENT DOCUMENTS

| | | | | |
|---|---|---|---|---|
| 4,355,331 A | * | 10/1982 | Georges | A61B 6/4266 348/E5.089 |
| 7,840,066 B1 | * | 11/2010 | Chen | G06T 5/002 382/168 |
| 2014/0050378 A1 | * | 2/2014 | Sengupta | G06T 11/008 382/131 |
| 2016/0171648 A1 | | 6/2016 | Thibault et al. | |

OTHER PUBLICATIONS

Kellner. T., "Revolution CT Scanner Sees Bones and Organs in Stunning Detail," GE Website, Available Online at https://www.ge.com/reports/post/107344100845/new-ct-scan-can-see-bones-and-organs-in-stunning/, Jan. 7, 2015, 13 pages.

* cited by examiner

*Primary Examiner* — Edward Park
(74) *Attorney, Agent, or Firm* — McCoy Russell LLP

(57) ABSTRACT

Methods and systems are provided for direct monochromatic image generation for spectral computed tomography. In one embodiment, a method comprises acquiring projection data during a scan of a subject, reconstructing a low energy image and a high energy image from the projection data, and generating a monochromatic image from the low energy image and the high energy image. In this way, a monochromatic image may be generated directly from low and high energy images with a substantial reduction in image noise, especially when compared to a monochromatic image generated indirectly from material density images.

18 Claims, 4 Drawing Sheets

US 10,383,589 B2

DIRECT MONOCHROMATIC IMAGE GENERATION FOR SPECTRAL COMPUTED TOMOGRAPHY

FIELD

Embodiments of the subject matter disclosed herein relate to non-invasive diagnostic imaging and non-destructive testing, and more particularly, to computed tomography (CT) imaging systems and methods for generating monochromatic images and reducing image noise variation as a function of x-ray energy.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

BRIEF DESCRIPTION

In one embodiment, a method comprises acquiring dual-energy projection data during a scan of a subject, reconstructing a low energy image and a high energy image from the projection data, and generating a monochromatic image from the low energy image and the high energy image. In this way, a monochromatic image may be generated directly from low and high energy images with a substantial reduction in image noise, especially when compared to a monochromatic image generated indirectly from material density images.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 4:
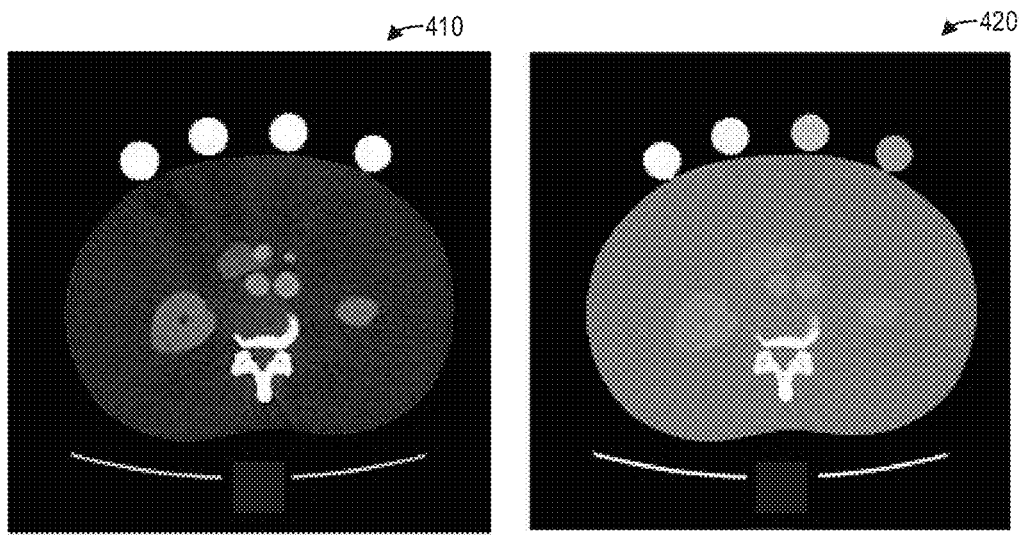
FIG. 4 shows multiple monochromatic images of a phantom generated using the method of FIG. 3 at different monochromatic energies.
Figure 5:
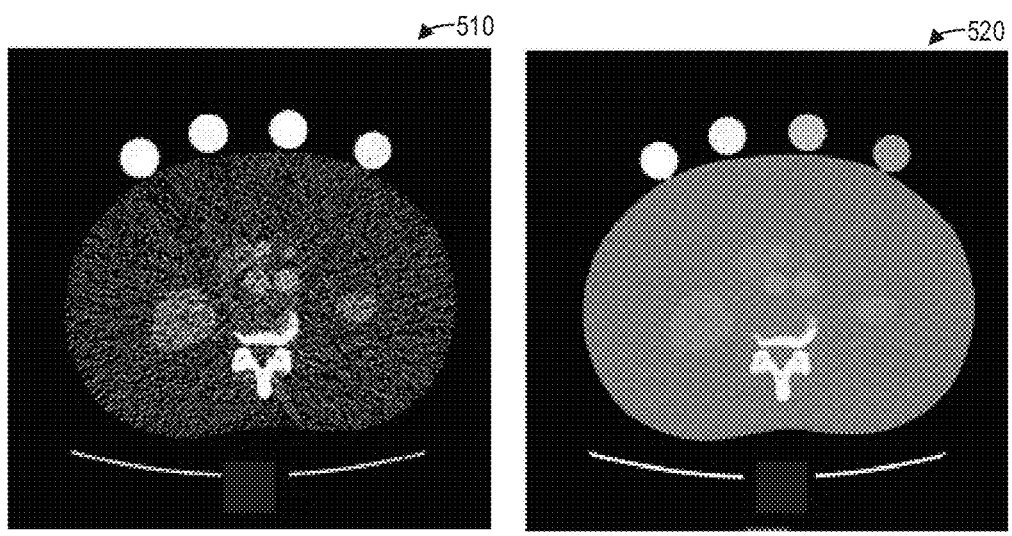
FIG. 5 shows multiple monochromatic images of the phantom generated using the traditional method at different monochromatic energies.
Figure 6:
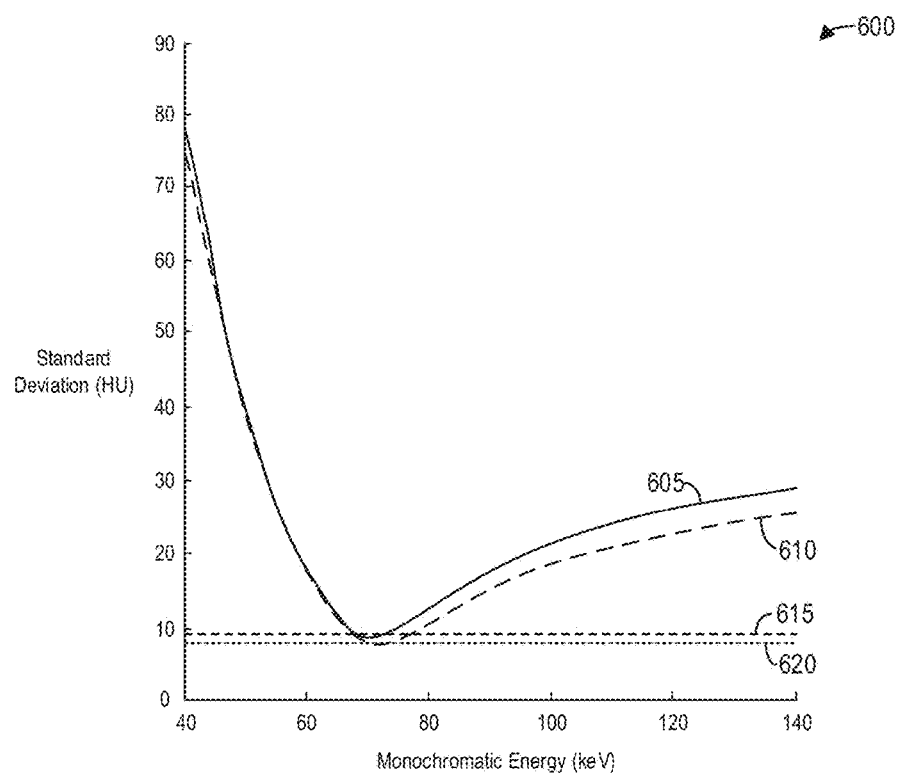
FIG. 6 shows a graph illustrating noise levels as a function of energy for the method of FIG. 3 in comparison to the traditional method.
Figure 7:
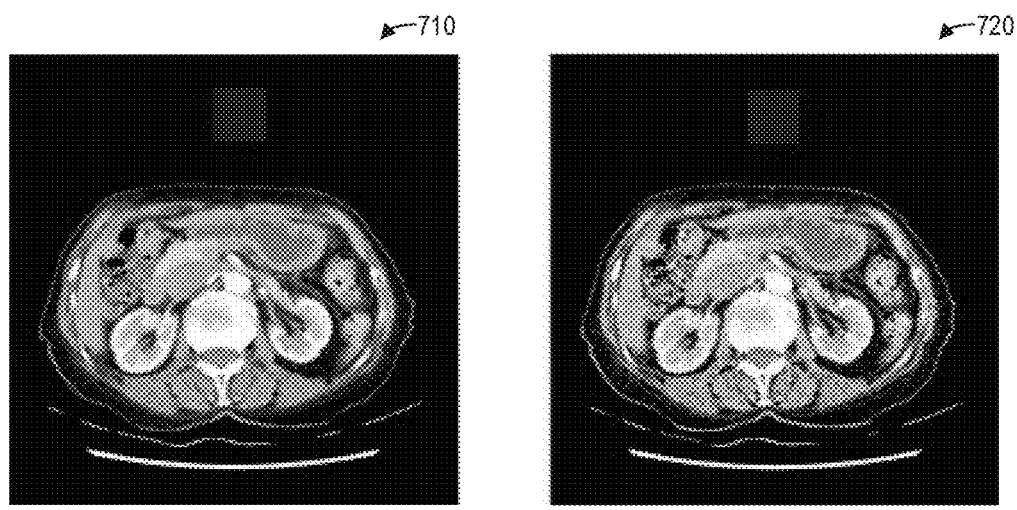
FIG. 7 shows clinical monochromatic images generated with the method of FIG. 3 and the traditional method.

The following description relates to various embodiments of medical imaging systems. In particular, systems and methods are provided for direct monochromatic image generation for spectral computed tomography (CT). An example of a CT imaging system that may be used to acquire images processed in accordance with the present techniques is provided in FIGS. 1 and 2. A method for generating monochromatic images, such as the method depicted in FIG. 3, may include generating a monochromatic image directly from high and low energy image reconstructions rather than from material basis images. FIG. 4 shows example monochromatic images of a phantom using the direct monochromatic image generation method depicted in FIG. 3, while FIG. 5 shows example monochromatic images of the same phantom using the indirect monochromatic image generation based on material basis images. The noise performance of the direct monochromatic image generation method is almost completely independent of the monochromatic energy, as shown in FIG. 6. The direct monochromatic image generation method also enables improved noise performance for clinical images, as shown in FIG. 7.

Though a CT system is described by way of example, it should be understood that the present techniques may also be useful when applied to images acquired using other imaging modalities, such as tomosynthesis, MM, C-arm angiography, and so forth. The present discussion of a CT imaging modality is provided merely as an example of one suitable imaging modality.

Dual or multi-energy spectral CT systems can reveal the densities of different materials in an object and generate images acquired at multiple monochromatic x-ray energy levels. In the absence of object scatter, a system derives the behavior at a different energy based on a signal from two regions of photon energy in the spectrum: the low-energy and the high-energy portions of the incident x-ray spectrum. In a given energy region of medical CT, two physical processes dominate the x-ray attenuation: Compton scattering and the photoelectric effect. The detected signals from two energy regions provide sufficient information to resolve the energy dependence of the material being imaged. Detected signals from the two energy regions provide sufficient information to determine the relative composition of an object composed of two hypothetical materials.

Different approaches have been developed to realize dual energy or spectral imaging. To name a few, dual x-ray source and detector, single x-ray source and detector with multiple acquisitions at different peak kilovoltage (kVp) or interleaved with fast kVp switching capability, and single x-ray source with an energy discriminative detector are leading techniques. In a single x-ray source and detector arrangement, a conventional third generation CT system may acquire projections sequentially at different kVp levels, which changes the peak and spectrum of energy of the incident photons comprising the emitted x-ray beams. Two scans are acquired, either back-to-back sequentially in time where the scans require two rotations around the subject, hereinafter referred to as rotate-rotate dual energy, or interleaved as a function of the rotation angle requiring one rotation around the subject, hereinafter referred to as fast-switching dual energy, in which the x-ray tube operates, for instance, at 80 kVp and 140 kVp potentials.

Typically, once dual or multi-energy data is obtained, a basis material decomposition (BMD) algorithm may be applied in order to image two distinct materials, such as water and iodine, as examples. A conventional BMD algorithm is based on the concept that, in an energy region for medical CT, the x-ray attenuation of any given material can be represented by a proper density mix of two materials with distinct x-ray attenuation properties, referred to as the basis materials. The BMD algorithm computes two material density images that represent the equivalent density of one of the basis materials based on the measured projections at high and low x-ray photon energy spectra, respectively. The material density images may be further converted to form monochromatic images at other desired monochromatic energies.

However, in the BMD approach described above (hereinafter referred to either as the traditional method or the indirect method of monochromatic image generation), the monochromatic images are formed based on the material basis images, and thus are generated indirectly from the originally acquired projection data. Special attention must be paid in the material density image generation process to ensure there is no significant mismatch between the treatments of the image generation process of the different basis materials. Significant mismatch of the material density images can lead to artifacts in the monochromatic images. Such requirements place significant constraints on the reconstruction process, especially in the de-noising process.

The systems and methods described herein address the issues mentioned above by enabling the direct generation of monochromatic images. Advantageously, the examples described herein reduce image noise variation as a function of x-ray energy.

Figure 1:
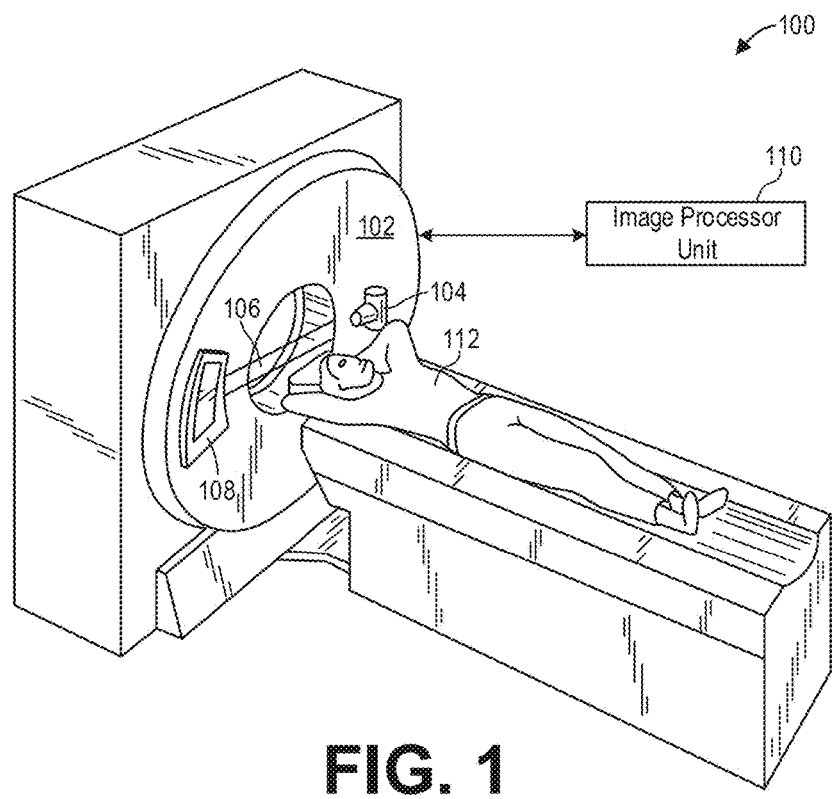
FIG. 1 shows a pictorial view of an imaging system according to an embodiment.

FIG. 1 illustrates an exemplary CT system 100 configured to allow fast and iterative image reconstruction. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray radiation source 104 configured to project a beam of x-ray radiation 106 for use in imaging the subject 112. Specifically, the x-ray radiation source 104 is configured to project the x-rays 106 towards a detector array 108 positioned on the opposite side of the gantry 102. Although FIG. 1 depicts only a single x-ray radiation source 104, in certain embodiments, multiple x-ray radiation sources and detectors may be employed to project a plurality of x-rays 106 for acquiring projection data corresponding to the patient at different energy levels. In some embodiments, the x-ray radiation source 104 may enable dual-energy gemstone spectral imaging (GSI) by rapid kVp switching. In some embodiments, the x-ray detector employed is a photon-counting detector which is capable of differentiating x-ray photons of different energies. In other embodiments, two sets of x-ray tube-detector are used to generate dual-energy projections, with one set at low-kVp and the other at high-kVp. This is often called dual-source system. In yet other embodiments, a conventional CT scanner is used in the so-called rotate-rotate mode with one fraction or full rotation collecting projections at low-kVp and the other at high-kVp. Such data collection can be carried out either in step-and-shoot mode or helical mode. Yet in another embodiment, twin filtration is used to modify the pre-patient x-ray beam in z so that one part has higher energy than the other part. When patient is index during the data acquisition, dual-energy projections are collected.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered backprojection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112.

In some known CT imaging system configurations, a radiation source projects a cone-shaped beam which is collimated to lie within an X-Y-Z plane of a Cartesian coordinate system and generally referred to as an "imaging plane." The radiation beam passes through an object being imaged, such as the patient or subject 112. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view." A "scan" of the object includes a set of views made at different gantry angles, or view angles, during one revolution of the radiation source and detector. It is contemplated that the benefits of the methods described herein accrue to medical imaging modalities other than CT, so as used herein the term view is not limited to the use as described above with respect to projection data from one gantry angle. The term "view" is used to mean one data acquisition whenever there are multiple data acquisitions from different angles, whether from a CT, PET, or SPECT acquisition, and/or any other modality including modalities yet to be developed as well as combinations thereof in fused embodiments.

The projection data is processed to reconstruct an image that corresponds to a two-dimensional slice taken through the object. One method for reconstructing an image from a set of projection data is referred to in the art as the filtered backprojection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Figure 2:
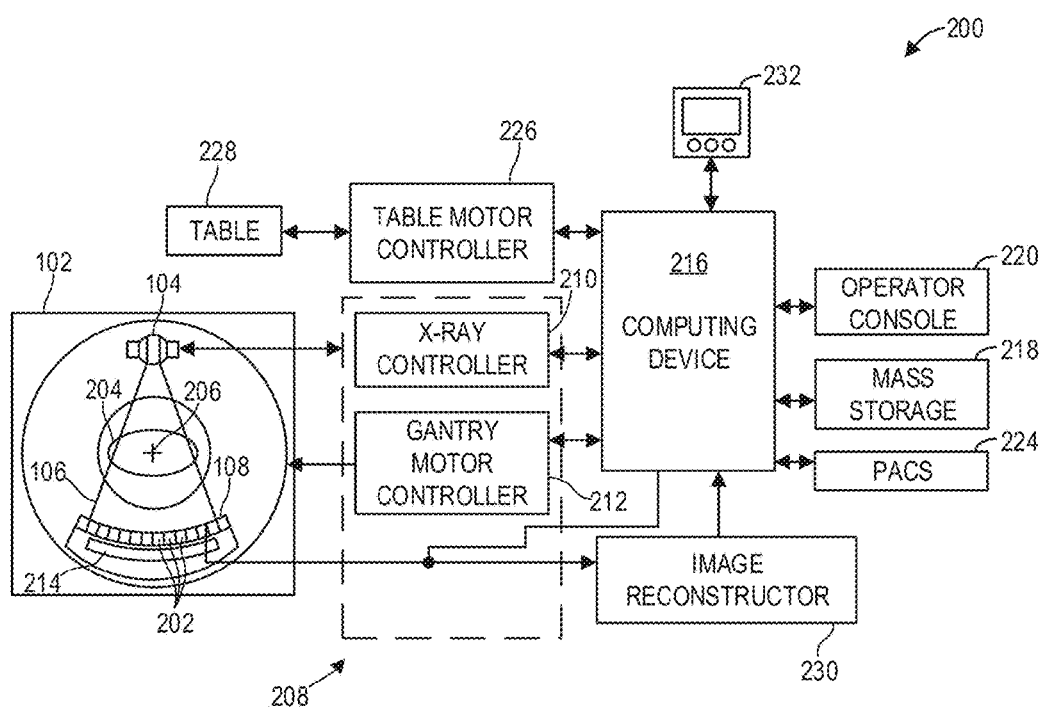
FIG. 2 shows a block schematic diagram of an exemplary imaging system according to an embodiment.

FIG. 2 illustrates an exemplary imaging system 200 similar to the CT system 100 of FIG. 1. In accordance with aspects of the present disclosure, the imaging system 200 is configured for direct monochromatic image generation. In one embodiment, the imaging system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In dual or multi-energy imaging, two or more sets of projection data are typically obtained for the imaged object at different tube kilovoltage (kVp) levels, which change the maximum and spectrum of energy of the incident photons comprising the emitted x-ray beams or, alternatively, at a single tube kilovoltage (kVp) level or spectrum with an energy resolving detector of the detector array 108.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of the two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computer or computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the imaging system 200 either includes or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 228 which may comprise a motorized table. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

The various methods and processes described further herein may be stored as executable instructions in non-transitory memory on a computing device in imaging system 200. In one embodiment, image reconstructor 230 may include such executable instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

Figure 3:
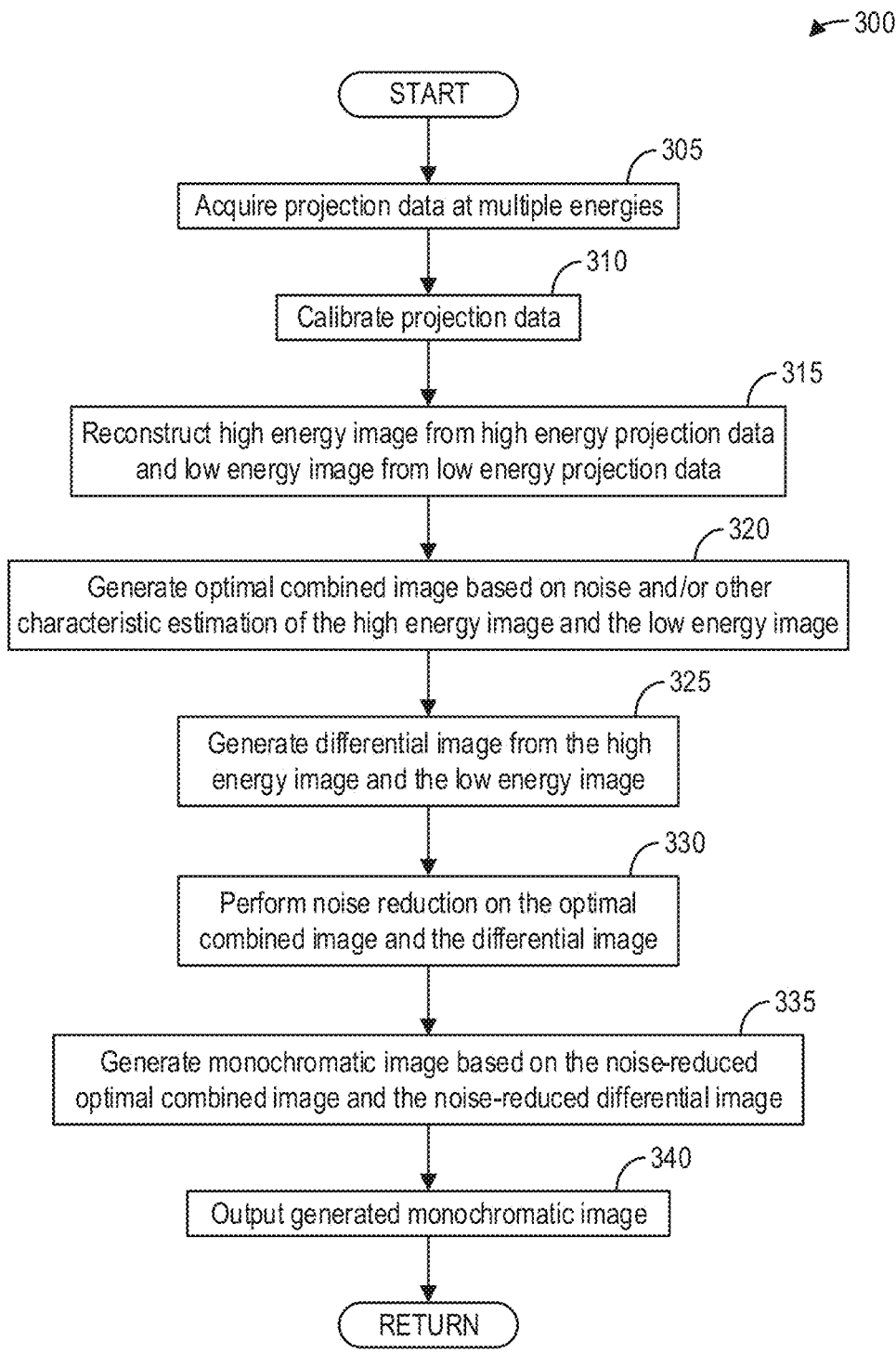
FIG. 3 shows a high-level flow chart illustrating an example method for generating monochromatic images according to an embodiment.

FIG. 3 shows a high-level flow chart illustrating an example method 300 for generating monochromatic images according to an embodiment. In particular, method 300 relates to generating one or more monochromatic images directly from high and low energy images. Method 300 may be carried out using the systems and components depicted in FIGS. 1 and 2, though it should be appreciated that method 300 may be implemented with other systems and components without departing from the scope of the present disclosure. Method 300 may be stored as executable instructions in non-transitory memory of a computing device, such as computing device 216.

Method 300 begins at 305. At 305, method 300 acquires projection data at multiple energies or peak tube kilovoltages (kVp). As non-limiting examples, method 300 may acquire projection data using any known dual-energy or multiple-energy imaging technique, including but not limited to fast-switching dual energy. The projection data therefore includes high energy projection data and low energy projection data. At 310, method 300 calibrates the acquired projection data, as discussed hereinabove with regard to FIG. 2.

Continuing at 315, method 300 reconstructs a high energy image from high energy projection data and a low energy image from low energy projection data. The high energy image may be denoted herein as $CT_H$ while the low energy image may be denoted herein as $CT_L$. The high energy image and the low energy image may be reconstructed using any suitable image reconstruction algorithm, including but not limited to filtered backprojection (FBP). Iterative reconstruction techniques, such as MBIR, can also be used to generate $CT_H$ and $CT_L$ at lower image noise.

At 320, method 300 generates an optimal combined image based on noise and/or other characteristic estimation(s) of the high energy image and the low energy image. Since the low and high energy images are acquired and reconstructed independently, noise in these images are not necessarily the same. If one wants to generate an optimal combined image in terms of noise, a weighted summation should be performed where the weights are determined by the variances of the two images. Thus, at 320, method 300 calculates noise scaling factors $\alpha$ and $\beta$ of the low energy image $CT_L$ and the high energy image $CT_H$, respectively. In some examples, the noise scaling factors $\alpha$ and $\beta$ comprise the variances of the low energy image $CT_L$ and the high energy image $CT_H$, respectively. It should be noted that the criteria used to generate an optimal combined image is not limited to noise. For example, contrast-to-noise ratio can be used to determine the noise scaling factors $\alpha$ and $\beta$. Additionally, minimization of image artifact can be used to determine the scaling factors as well.

Thus, method 300 generates an optimal combined image $CT_C$ from the high energy image $CT_H$, the low energy image $CT_L$, and the calculated noise scaling factors $\alpha$ and $\beta$:

$$CT_C = \alpha \cdot CT_L + \beta \cdot CT_H.$$

At 335, method 300 generates a differential image $CT_D$ from the high energy image $CT_H$ and the low energy image $CT_L$. Specifically, the differential image $CT_D$ comprises the difference between the low energy image $CT_L$ and the high energy image $CT_H$:

$$CT_D = CT_L - CT_H.$$

Continuing at 330, method 300 performs noise reduction on the optimal combined image and the differential image to obtain a noise-reduced differential image and a noise-reduced optimal combined image. Additional noise suppression or reduction can be applied to either or both $CT_C$ and $CT_D$. A variety of suitable image processing techniques for noise reduction may be applied.

At 335, method 300 generates a monochromatic image $CT_M$ based on the noise-reduced differential image $CT_D$, the noise-reduced optimal combined image $CT_C$, and one or more calculated coefficients.

In one example, the method 300 calculates the one or more coefficients based on attenuation coefficients. The CT attenuation $f_L$ generated with the low energy projection data is related to the low energy image $CT_L$ by the expression:

$$f_L \left( \frac{CT_L}{1000} + 1 \right) \cdot \mu_{WL},$$

where $\mu_{WL}$ comprises the attenuation coefficient of water at a low mean keV. Similarly, the CT attenuation $f_H$ generated with the high energy projection data is related to the high energy image $CT_H$ by the expression:

$$f_H = \left(\frac{CT_H}{1000} + 1\right) \cdot \mu_{WH},$$

where $\mu_{WH}$ comprises the attenuation coefficient of water at a high mean keV. A water density image $f_W$ is related to the attenuations $f_L$ and $f_H$ by the expression:

$$f_W = \frac{\mu_{IH} \cdot f_L - \mu_{IL} \cdot f_H}{\mu_{WL} \cdot \mu_{IH} - \mu_{WH} \cdot \mu_{IL}},$$

where $\mu_{IH}$ comprises the attenuation coefficient of iodine at the high mean keV, and $\mu_{IL}$ comprises the attenuation coefficient of iodine at the low mean keV. Similarly, an iodine density image $f_I$ is related to the attenuations $f_L$ and $f_H$ by the expression:

$$f_I = \frac{\mu_{WL} \cdot f_H - \mu_{WH} \cdot f_L}{\mu_{WL} \cdot \mu_{IH} - \mu_{WH} \cdot \mu_{IL}}.$$

A monochromatic attenuation image $f_M$ at M keV may then be expressed as:

$$f_M = \mu_{WM} f_W + \mu_{IM} f_I.$$

In terms of CT numbers, it can be shown that $$CT_M = \frac{f_M - \mu_{WM}}{\mu_{WM}} \cdot 1000$$

Substituting the above expressions into the expression for $CT_M$ yields the expression:

$$CT_M = \frac{(\mu_{IH} \cdot \mu_{WM} - \mu_{WH} \cdot \mu_{IM}) \cdot \mu_{WL}}{(\mu_{WL} \cdot \mu_{IH} - \mu_{WH} \cdot \mu_{IL}) \cdot \mu_{WM}} \cdot CT_L + \frac{(\mu_{WL} \cdot \mu_{IM} - \mu_{IL} \cdot \mu_{WM}) \cdot \mu_{WH}}{(\mu_{WL} \cdot \mu_{IH} - \mu_{WH} \cdot \mu_{IL}) \cdot \mu_{WM}} \cdot CT_H.$$

This expression can be simplified into:

$$CT_M = \varphi_L \cdot CT_L + \varphi_H \cdot CT_H,$$

where the coefficients are defined as:

$$\varphi_L = \frac{(\mu_{IH} \cdot \mu_{WM} - \mu_{WH} \cdot \mu_{IM}) \cdot \mu_{WL}}{(\mu_{WL} \cdot \mu_{IH} - \mu_{WH} \cdot \mu_{IL}) \cdot \mu_{WM}},$$

and $$\varphi_H = \frac{(\mu_{WL} \cdot \mu_{IM} - \mu_{IL} \cdot \mu_{WM}) \cdot \mu_{WH}}{(\mu_{WL} \cdot \mu_{IH} - \mu_{WH} \cdot \mu_{IL}) \cdot \mu_{WM}}.$$

Referring again to FIG. 3, method 300 calculates one or more coefficients $\varphi_L$ and $\varphi_H$ based on attenuation coefficients, as discussed above. In some examples, method 300 only calculates the coefficient $\varphi_L$.

By utilizing the property that $\varphi_L + \varphi_H = 1$ and $\alpha + \beta = 1$, the expression described above for a monochromatic image $CT_M$ may be expressed in terms of the combined image $CT_C$ and the differential image $CT_D$:

$$CT_M = CT_C + (\varphi_L - \alpha) \cdot CT_D.$$

Thus, method 300 generates the monochromatic image $CT_M$ via the weighted summation of the optimal combined image and the differential image.

In some examples, the monochromatic image $CT_M$ may be generated directly from the low energy image $CT_L$ and the high energy image $CT_H$. As noted above, the monochromatic image $CT_M$ is the linear combination of the combined image $CT_C$ and the differential image $CT_D$. Furthermore, as noted above, the combined image $CT_C$ and the differential image $CT_D$ are the linear combinations of the low energy image $CT_L$ and the high energy image $CT_H$. Therefore, the monochromatic image $CT_M$ can be generated directly from the low energy image $CT_L$ and the high energy image $CT_H$. Note that $CT_M$ can be expressed as a linear combination of the low energy image $CT_L$ and the high energy image $CT_H$:

$$CT_M = CT_C + (\varphi_L - \alpha) \cdot CT_D = \alpha \cdot CT_L + \beta \cdot CT_H + (\varphi_L - \alpha) \cdot (CT_L - CT_H).$$

In other examples, the monochromatic image $CT_M$ may be reconstructed directly from the low energy projection data and the high energy projection data. As noted above, the low energy image $CT_L$ and the high energy image $CT_H$ are reconstructed from the low energy projection data and the high energy projection data respectively. Therefore, the monochromatic image $CT_M$ can be reconstructed directly from the low energy projection data and high energy projection data directly if the reconstruction process is linear. For FBP and many hybrid reconstruction algorithms, the assumption of a linear reconstruction process is valid.

At 340, method 300 outputs the generated monochromatic image $CT_M$. The monochromatic image may be output, for example, to a display device, such as display 232, for review by a physician or radiologist. Additionally or alternatively, the monochromatic image may be output to a memory, such as mass storage 218, or to PACS 224, for subsequent retrieval and review. Method 300 then returns.

The equation above for the monochromatic image $CT_M$ indicates that the noise in the monochromatic image $CT_M$ is contributed by two terms. The first term is the optimal combined image $CT_C$ and is energy independent. That is, the noise contribution from the first term does not change whether the monochromatic image is at 40 keV or at 80 keV, as an example. Note that in dual-energy applications, monochromatic images can be generated at any keV. For example, for some dual-energy imaging systems, monochromatic images can be generated from 40 keV to 140 keV at 1 keV increments. The noise contribution from the first term does not change over all keVs. The second term contributes to the keV-dependent noise characteristics of the monochromatic image. Thus, if the noise in the second term can be suppressed to nearly zero, a nearly constant noise over all keVs may be achieved.

FIGS. 4 and 5 illustrate the improved noise performance of the method described herein for generating monochromatic images. In particular, FIG. 4 shows a first monochromatic image 410 at a first energy and a second monochromatic image 420 at a second energy, while FIG. 5 shows a third monochromatic image 510 at the first energy and a fourth monochromatic image 520 at the second energy. The first monochromatic image 410 and the second monochromatic image 420 were generated using the method 300 described hereinabove, also referred to herein as the direct monochromatic image generation method. In contrast, the third monochromatic image 510 and the fourth monochromatic image 520 were generated with the traditional or indirect monochromatic image generation method using water and iodine images. All of the images depict a same Kyoto body phantom (depicted as the fabiform object in the images) with multiple iodine rods (depicted as four circles adjacent to the body phantom). The first energy is 40 keV and the second energy is 80 keV. No additional noise reduction method was utilized for any of the images. The images 410 and 420 generated with the direct monochromatic image generation method show little dependency on x-ray energy. In contrast, the third monochromatic image 510 shows that the indirect monochromatic image generation method performs poorly at 40 keV, especially in comparison to the first monochromatic image 410.

FIG. 6 shows a graph 600 including a plurality of plots illustrating standard deviation, measured in Hounsfield units, as a function of monochromatic energy, measured in keV, for two regions of interest (ROIs) of the phantom study discussed hereinabove with regard to FIGS. 4 and 5. The first ROI is located within the body phantom and the second ROI is located with one of the iodine rods.

In particular, plot 605 and plot 610 depict the standard deviation as a function of monochromatic energy in a first ROI and a second ROI, respectively, for the traditional method for monochromatic image generation using water and iodine images. Plot 615 and plot 620 depict the standard deviation as a function of monochromatic energy in the first ROI and the second ROI, respectively, for the direct method for monochromatic image generation described herein.

As depicted, the noise performance of the images generated using the indirect method is substantially worse than the noise performance of the images generated using the direct method at 40 keV. In this way, FIG. 6 quantitatively confirms what is visually apparent when comparing the first image 410 and the third image 510.

Further, the noise performance of the images generated using the indirect method is comparable to the noise performance of the images generated using the direct method at 80 keV. This confirms what is visually apparent when comparing the second image 420 to the fourth image 520.

Although the indirect method has acceptable noise performance around 70 keV, as depicted by plots 605 and 610, the noise performance of the direct method is nearly independent of the keV, as depicted by plots 615 and 620.

As additional evidence of the superiority in noise performance of the direct monochromatic image generation method over the indirect monochromatic image generation method, FIG. 7 shows two monochromatic images 710 and 720 of a clinical study, where the monochromatic energy is 40 keV and the images are generated from data acquired during an abdominal scan with GSI. In particular, the monochromatic image 710 is generated using the direct method described hereinabove with regard to FIG. 3, whereas the monochromatic image 720 is generated using the traditional method. It is visually evident that the monochromatic image 710 is less noisy than the monochromatic image 720, as the monochromatic image 710 is smoother (i.e., has fewer textural variations within different regions of the imaged abdomen) than the monochromatic image 720.

A technical effect of the disclosure is the generation of a monochromatic image directly from high and low energy images. Another technical effect of the disclosure is the generation of a monochromatic image with a substantial noise reduction regardless of a given monochromatic energy.

Yet another technical effect of the disclosure is the generation of a monochromatic image without performing basis material decomposition. Another technical effect of the disclosure is the display of a monochromatic image with reduced image noise.

In one embodiment, a method comprises acquiring projection data during a scan of a subject, reconstructing a low energy image and a high energy image from the projection data, and generating a monochromatic image from the low energy image and the high energy image.

In a first example of the method, the method further comprises generating a combined image from the low energy image and the high energy image, and generating a differential image from the low energy image and the high energy image, wherein the monochromatic image is generated from the combined image and the differential image. In a second example of the method optionally including the first example, generating the differential image comprises subtracting the high energy image from the low energy image to generate the differential image. In a third example of the method optionally including one or more of the first and the second examples, generating the combined image comprises producing a weighted summation of the low energy image and the high energy image. In a fourth example of the method optionally including one or more of the first through third examples, the weighted summation is weighted by variances ratios of the low energy image and the high energy image. In a fifth example of the method optionally including one or more of the first through fourth examples, generating the monochromatic image from the combined image and the differential image comprises summing the combined image and the differential image, wherein the differential image is weighted by at least one of the variances ratios. In a sixth example of the method optionally including one or more of the first through fifth examples, the method further comprises calculating a coefficient based on a selected monochromatic energy, a mean low energy, and a mean high energy, wherein the differential image is further weighted by the coefficient, and wherein the monochromatic image is at the selected monochromatic energy. In a seventh example of the method optionally including one or more of the first through sixth examples, the method further comprises outputting the monochromatic image to one or more of a display device and a storage device. In an eighth example of the method optionally including one or more of the first through seventh examples, the method further comprises performing noise reduction on the differential image. In a ninth example of the method optionally including one or more of the first through eighth examples, the method further comprises performing noise reduction to both the combined image and the differential image.

In another embodiment, a method comprises acquiring projection data including high energy projection data acquired at a high energy and low energy projection data acquired at a low energy, and generating a monochromatic image at a monochromatic energy from the projection data.

In a first example of the method, the monochromatic image is generated directly from the projection data without intermediate reconstructions. In a second example of the method, generating the monochromatic image at the monochromatic energy from the projection data comprises generating a combined image from the high energy projection data and the low energy projection data, generating a differential image from the high energy projection data and the low energy projection data, and generating the monochromatic image at the monochromatic energy from the combined image and the differential image. In a third example of the method optionally including one or more of the first and second examples, the combined image and the differential image are generated directly from the high energy projection data and the low energy projection data. In a fourth example of the method optionally including one or more of the first through third examples, the method further comprises reconstructing a high energy image from the high energy projection data and a low energy image from the low energy projection data, wherein generating the combined image from the high energy projection data and the low energy projection data comprises generating the combined image from the high energy image and the low energy image, and wherein generating the differential image from the high energy projection data and the low energy projection data comprises generating the differential image from the high energy image and the low energy image. In a fifth example of the method optionally including one or more of the first through fourth examples, the method further comprises calculating noise scaling factors of the high energy image and the low energy image. In a sixth example of the method optionally including one or more of the first through fifth examples, generating the combined image from the high energy image and the low energy image comprises summing the high energy image and the low energy image, wherein the high energy image and the low energy image are weighted respectively by the noise scaling factors. In a seventh example of the method optionally including one or more of the first through sixth examples, the method further comprises calculating a coefficient based on a plurality of attenuation coefficients, wherein generating the monochromatic image from the combined image and the differential image comprises summing the combined image and the differential image, wherein the differential image is weighted based on the coefficient and at least one noise scaling factor of the noise scaling factors. In an eighth example of the method optionally including one or more of the first through seventh examples, the plurality of attenuation coefficients includes an attenuation coefficient of iodine at a mean low energy of the low energy, an attenuation coefficient of iodine at a mean high energy of the high energy, an attenuation coefficient of iodine at the monochromatic energy, an attenuation coefficient of water at the mean low energy, an attenuation coefficient of water at the mean high energy, and an attenuation coefficient of water at the monochromatic energy. In a ninth example of the method optionally including one or more of the first through eighth examples, generating the differential image comprises subtracting the high energy image from the low energy image to generate the differential image.

In yet another embodiment, a system comprises an x-ray source that emits a beam of x-rays toward an object to be imaged, a detector that receives the x-rays attenuated by the object, a data acquisition system (DAS) operably connected to the detector, and a computing device operably connected to the DAS and configured with executable instructions in non-transitory memory that when executed cause the computing device to: acquire, via the DAS, projection data during a scan of the object; reconstruct a low energy image and a high energy image from the projection data; and generate a monochromatic energy from the low energy image and the high energy image.

In a first example of the system, the computing device is further configured with executable instructions in the non-transitory memory that when executed cause the computing device to generate a combined image from the low energy image and the high energy image, and generate a differential image from the low energy image and the high energy image, wherein the monochromatic image is generated from the combined image and the differential image. In a second example of the system optionally including the first example, generating the differential image comprises subtracting the high energy image from the low energy image to generate the differential image, and wherein generating the combined image comprises producing a weighted summation of the low energy image and the high energy image. In a third example of the system optionally including one or more of the first and the second examples, generating the monochromatic image from the combined image and the differential image comprises summing the combined image and the differential image, wherein the differential image is weighted by a variance of one of the high energy image and the low energy image. In a fourth example of the system optionally including one or more of the first through third examples, the computing device is further configured with executable instructions in the non-transitory memory that when executed cause the computing device to calculate a coefficient based on a monochromatic energy, a mean low energy, and a mean high energy, wherein the differential image is further weighted by the coefficient, and wherein the monochromatic image is at the monochromatic energy. In a fifth example of the system optionally including one or more of the first through fourth examples, the system further comprises a display device communicatively coupled to the computing device, wherein the computing device is further configured with instructions in the non-transitory memory that when executed cause the computing device to output the monochromatic image to the display device.

In another embodiment, a method comprises acquiring projection data including high energy projection data acquired at a high energy and low energy projection data acquired at a low energy, reconstructing a combined image directly from the high energy projection data and low energy projection data, reconstructing a differential image directly from the high energy projection data and the low energy projection data, and generating a monochromatic image at a monochromatic energy from the combined image and the differential image.

In yet another embodiment, a method comprises acquiring projection data including high energy projection data acquired at a high energy and low energy projection data acquired at a low energy, and reconstructing a monochromatic image directly from the high energy projection data and the low energy projection data.

In another representation, a method comprises acquiring projection data including high energy projection data acquired at a high energy and low energy projection data acquired at a low energy, generating a combined image from the high energy projection data and the low energy projection data, generating a differential image from the high energy projection data and the low energy projection data, and generating a monochromatic image at a monochromatic energy from the combined image and the differential image.

In a first example of the method, the combined image and the differential image are generated directly from the high energy projection data and the low energy projection data. In a second example of the method, the method further comprises reconstructing a high energy image from the high energy projection data and a low energy image from the low energy projection data, wherein generating the combined image from the high energy projection data and the low energy projection data comprises generating the combined image from the high energy image and the low energy image, and wherein generating the differential image from the high energy projection data and the low energy projection data comprises generating the differential image from the high energy image and the low energy image. In a third example of the method optionally including one or more of the first and second examples, the method further comprises calculating noise scaling factors of the high energy image and the low energy image. In a fourth example of the method optionally including one or more of the first through third examples, generating the combined image from the high energy image and the low energy image comprises summing the high energy image and the low energy image, wherein the high energy image and the low energy image are weighted respectively by the noise scaling factors. In a fifth example of the method optionally including one or more of the first through fourth examples, the method further comprises calculating a coefficient based on a plurality of attenuation coefficients, wherein generating the monochromatic image from the combined image and the differential image comprises summing the combined image and the differential image, wherein the differential image is weighted based on the coefficient and at least one noise scaling factor of the noise scaling factors. In a sixth example of the method optionally including one or more of the first through fifth examples, the plurality of attenuation coefficients includes an attenuation coefficient of iodine at a mean low energy of the low energy, an attenuation coefficient of iodine at a mean high energy of the high energy, an attenuation coefficient of iodine at the monochromatic energy, an attenuation coefficient of water at the mean low energy, an attenuation coefficient of water at the mean high energy, and an attenuation coefficient of water at the monochromatic energy. In a seventh example of the method optionally including one or more of the first through sixth examples, generating the differential image comprises subtracting the high energy image from the low energy image to generate the differential image.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. Although the examples provided herein are related to medical application, the scope of the present disclosure covers non-destructive testing in industrial, biomedical, and other fields. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
acquiring projection data during a scan of a subject;
reconstructing a low energy image and a high energy image from the projection data;
generating a combined image from the low energy image and the high energy image;
generating a differential image from the low energy image and the high energy image; and
generating a monochromatic image from the combined image and the differential image.

2. The method of claim 1, wherein generating the differential image comprises subtracting the high energy image from the low energy image to generate the differential image.

3. The method of claim 1, wherein generating the combined image comprises producing a weighted summation of the low energy image and the high energy image, wherein the weighted summation is weighted by variances of the low energy image and the high energy image.

4. The method of claim 3, wherein generating the monochromatic image from the combined image and the differential image comprises summing the combined image and the differential image, wherein the differential image is weighted by at least one of the variances.

5. The method of claim 4, further comprising calculating a coefficient based on a selected monochromatic energy, a mean low energy, and a mean high energy, wherein the differential image is further weighted by the coefficient, and wherein the monochromatic image is at the selected monochromatic energy.

6. The method of claim 1, wherein the monochromatic image is generated directly from the low energy image and the high energy image.

7. A method, comprising:
acquiring projection data including high energy projection data acquired at a high energy and low energy projection data acquired at a low energy;
generating a combined image from the high energy projection data and the low energy projection data;
generating a differential image from the high energy projection data and the low energy projection data; and
generating a monochromatic image at a monochromatic energy from the combined image and the differential image.

8. The method of claim 7, wherein the combined image and the differential image are generated directly from the high energy projection data and the low energy projection data.

9. The method of claim 7, further comprising reconstructing a high energy image from the high energy projection data and a low energy image from the low energy projection data, wherein generating the combined image from the high energy projection data and the low energy projection data comprises generating the combined image from the high energy image and the low energy image, and wherein generating the differential image from the high energy projection data and the low energy projection data comprises generating the differential image from the high energy image and the low energy image.

10. The method of claim 9, further comprising calculating noise scaling factors of the high energy image and the low energy image.

11. The method of claim 10, wherein generating the combined image from the high energy image and the low energy image comprises summing the high energy image and the low energy image, wherein the high energy image and the low energy image are weighted respectively by the noise scaling factors.

12. The method of claim 10, further comprising calculating a coefficient based on a plurality of attenuation coefficients, wherein generating the monochromatic image from the combined image and the differential image comprises summing the combined image and the differential image, wherein the differential image is weighted based on the coefficient and at least one noise scaling factor of the noise scaling factors.

13. The method of claim 12, wherein the plurality of attenuation coefficients includes an attenuation coefficient of iodine at a mean low energy of the low energy, an attenuation coefficient of iodine at a mean high energy of the high energy, an attenuation coefficient of iodine at the monochromatic energy, an attenuation coefficient of water at the mean low energy, an attenuation coefficient of water at the mean high energy, and an attenuation coefficient of water at the monochromatic energy.

14. The method of claim 9, wherein generating the differential image comprises subtracting the high energy image from the low energy image to generate the differential image.

15. A system, comprising:
an x-ray source that emits a beam of x-rays toward an object to be imaged;
a detector that receives the x-rays attenuated by the object;
a data acquisition system (DAS) operably connected to the detector; and
a computing device operably connected to the DAS and configured with executable instructions in non-transitory memory that when executed cause the computing device to:
acquire, via the DAS, projection data during a scan of the object;
reconstruct a low energy image and a high energy image from the projection data;
generate a combined image from the low energy image and the high energy image;
generate a differential image from the low energy image and the high energy image; and
generate a monochromatic image at a monochromatic energy from the combined image and the differential image.

16. The system of claim 15, wherein the monochromatic image is generated from the combined image and the differential image by summing the combined image and the differential image, wherein the differential image is weighted by a variance of one of the high energy image and the low energy image.

17. The system of claim 16, wherein the computing device is further configured with executable instructions in the non-transitory memory that when executed cause the computing device to calculate a coefficient based on the monochromatic energy, a mean low energy, and a mean high energy, wherein the differential image is further weighted by the coefficient, and wherein the monochromatic image is at the monochromatic energy.

18. A method, comprising:
acquiring projection data including high energy projection data acquired at a high energy and low energy projection data acquired at a low energy;
generating a differential image and a combined image directly from the projection data; and
reconstructing a monochromatic image directly from the differential image and the combined image.

* * * * *